United States Patent [19]

Gouda

[11] Patent Number: 4,977,887
[45] Date of Patent: Dec. 18, 1990

[54] ENDOSCOPE WITH SCOPE SECTION OF ADJUSTABLE RIGIDITY

[75] Inventor: Kazuhiko Gouda, Tochigi, Japan

[73] Assignee: Kabushiki Kaisha Toshiba, Kawasaki, Japan

[21] Appl. No.: 513,977

[22] Filed: Apr. 24, 1990

[30] Foreign Application Priority Data

May 2, 1989 [JP] Japan .................................. 1-113373

[51] Int. Cl.⁵ .............................................. A61B 1/00
[52] U.S. Cl. ...................................................... 128/4
[58] Field of Search ........................................... 128/4

[56] References Cited

U.S. PATENT DOCUMENTS

| | | | |
|---|---|---|---|
| 3,948,251 | 4/1976 | Hosono | 128/4 |
| 4,024,858 | 5/1977 | Chikama | 128/4 |
| 4,329,980 | 5/1982 | Terada | 128/4 |
| 4,805,545 | 2/1989 | Kanbara | 128/4 |

Primary Examiner—William H. Grieb
Attorney, Agent, or Firm—Foley & Lardner, Schwartz, Jeffery, Schwaab, Mack, Blumenthal & Evans

[57] ABSTRACT

An endoscope capable of adjustably changing the rigidity of the middle portion of the scope section. The endoscope include a middle portion constructed by using a composite helical tube formed by outer and inner helical tubes of different winding radii which are wound coaxially, and a controller for controlling a rigidity of the middle portion by changing a winding radius of the inner helical tube while the outer helical tube is immovably fixed. The outer and inner helical tubes are preferably wound at the same winding pitch in the same winding direction, and arranged such that each winding loop of each one of the outer and inner helical tubes is facing a clearance between adjacent winding loops of another one of the outer and inner helical tube.

12 Claims, 7 Drawing Sheets

ENDOSCOPE WITH SCOPE SECTION OF ADJUSTABLE RIGIDITY

BACKGROUND OF THE INVENTION

1. Field of the Invention

The present invention relates to an endoscope to be inserted into a patient, in order to facilitate an observation inside the body cavity of the patient.

2. Description of the Background Art

In inserting a scope section of an endoscope into the body cavity of a patient, an operator is required to perform highly elaborated maneuvering of the endoscope in order to lead an end portion of the scope section, on which an imaging device is mounted, to a region of interest, while bending a middle portion of the scope section along the shape of the body cavity.

Also, in moving the scope section from one region of interest to another region of interest, the similar maneuvering of the endoscope is required.

In particular, the insertion of the scope section into various parts of the large intestine is known to require a difficult maneuvering of the endoscope. This is because the large intestine involve many portions which are curving in complicated manner, such as the sigmoid colon, the curving portion around the spleen, the transverse colon, and the curving portion around the liver.

Figure 1:
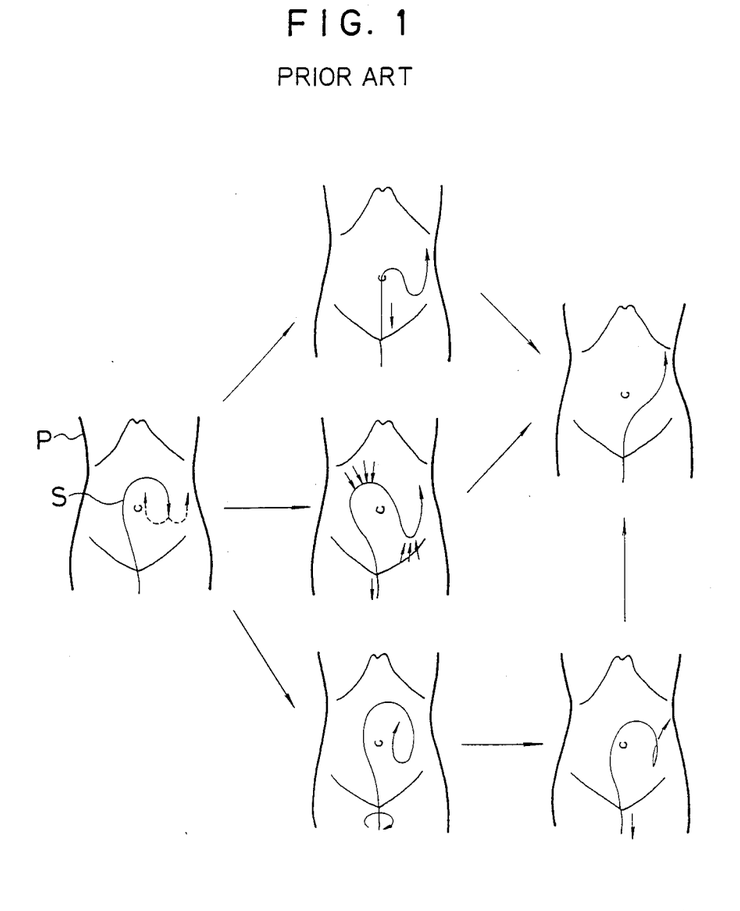
FIG. 1 is a sequential illustration of the known procedure for inserting a scope section of an endoscope into a portion between the sigmoid colon and the descending colon of a patient.

For example, in FIG. 1, a procedure for inserting the scope section S into a portion between the sigmoid colon and descending color of a patient P is depicted in sequence. As can be seen from FIG. 1, the maneuvering required in such a case is quite complex, and can become even more sophisticated when an attempt is made to reduce the pain of the patient as much as possible.

In view of such a severe demand made on the operator, it is considered desirable to give as much of control of movements of the scope section as possible to the operator. In particular, in a course of elaborated operation of the endoscope such as that shown in FIG. 1, there are many occasions in which the middle portion of the scope section is desired to be stiff, while there are many other occasions in which the middle portion of the scope section is desired to be flexible.

However, in a conventional endoscope, a rigidity of the middle portion of the scope section is fixed and not adjustable, so that the maneuvering by the operator has been receiving a considerable limitation with regards the rigidity of the scope section.

SUMMARY OF THE INVENTION

It is therefore an object of the present invention to provide an endoscope capable of adjustably changing the rigidity of the middle portion of the scope section.

According to one aspect of the present invention there is provided an endoscope equipped with a scope section to be inserted into a body cavity of a patient, the scope section comprising: an end portion having an imaging device; a middle portion connected to the end portion, comprising: a composite helical tube formed by outer and inner helical tubes of different winding radii which are wound coaxially; and an outer covering wrapped around the composite helical tube; and means for controlling a rigidity of the middle portion by changing a winding radius of the inner helical tube while the outer helical tube is immovably fixed.

According to another aspect of the present invention there is provided an endoscope equipped with a scope section to be inserted into a body cavity of a patient, the scope section comprising: an end portion having an imaging device; a middle portion connected to the end portion, comprising: a composite helical tube formed by more than one helical tubes of different winding radii which are wound coaxially; and an outer covering wrapped around the composite helical tube; and means for controlling a rigidity of the middle portion by changing a winding radius of each helical tube other than an outermost helical tube while the outermost helical tube is immovably fixed.

Other features and advantages of the present invention will become apparent from the following description taken in conjunction with the accompanying drawings.

DETAILED DESCRIPTION OF THE PREFERRED EMBODIMENTS

Figure 2:
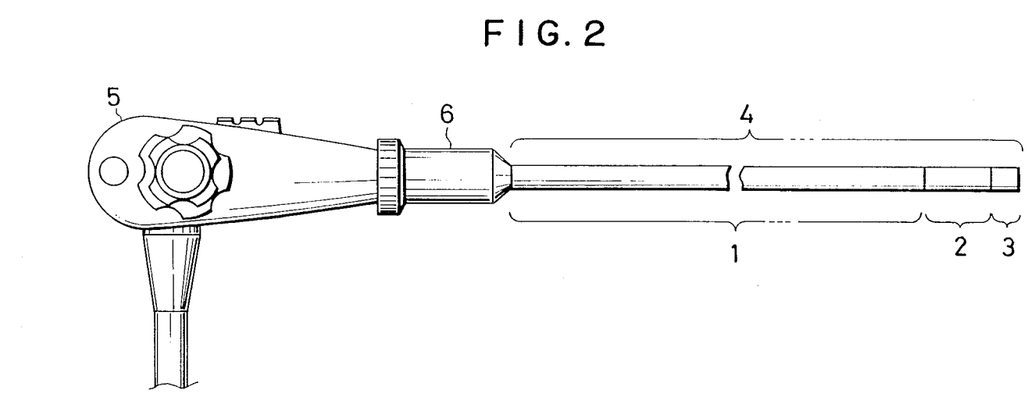
FIG. 2 is a side view of a scope section of one embodiment of an endoscope according to the present invention.

Referring now to FIG. 2, there is shown a scope section of one embodiment of an endoscope according to the present invention.

In this embodiment, the scope section comprises an insertion portion 4 including a middle portion 1, a bending portion 2, and an end portion 3, a scope grip portion 5, and a rigidity controller 6 located between the insertion portion 4 and the scope grip portion 5. A detail mechanism of the rigidity controller 6 will be described below.

Now, according to the present invention, the rigidity of the middle portion 1 is made to be adjustably changeable. This is achieved by constructing the middle portion 1 as follows.

Figure 3:
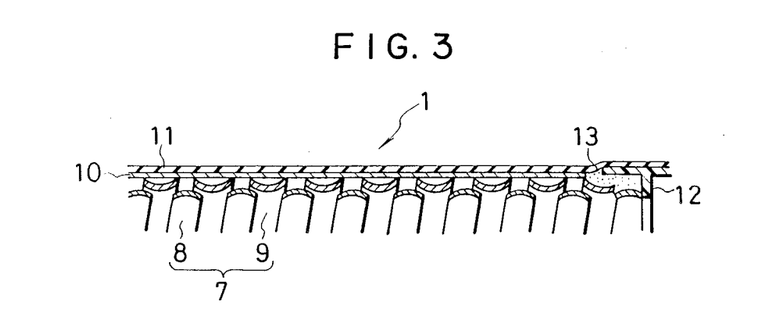
FIG. 3 is an enlarged cross sectional view of a part of a middle portion of the scope section of FIG. 2 in a soft state.

Namely, as shown in FIG. 3, the middle portion 1 is constructed from a composite helical tube 7 comprising an inner helical tube 8 and an outer helical tube 9 having a radius larger than that of the inner helical tube 8 which is wound around the inner helical tube 8, a blade 10 wrapped around the composite helical tube 7, and an outer rubber covering 11 to form an outer surface of the middle portion 1 which is wrapped around the blade 10.

The inner helical tube 8 and the outer helical tube 9 preferably are wound coaxially at the same winding pitch in the same winding direction, with each winding loop of each of the inner helical tube 8 and the outer helical tube 9 facing a clearance between adjacent winding loops of the other, i.e., with the inner helical tube 8 and the outer helical tube 9 displaced by a half of their common winding pitch.

Furthermore, preferably, the inner helical tube 8 is made of a curved wiring piece having its convex side facing toward the outer helical tube 9, while the outer helical tube 9 is made of a curved wiring piece having its convex side facing toward the inner helical tube 8, as shown in FIG. 3.

Such inner helical tube 8 and outer helical tube 9 can be manufactured from a flexible metal wiring piece.

At a front end of the middle portion 1 neighboring the bending portion 2, the inner helical tube 8, the outer helical tube 9, and the blade 10 are fixed to a connector piece 12 at a fixing portion 13, where the fixation at the fixing portion 13 can be achieved by any of adhering, welding, or soldering.

On the other hand, at a rear end of the middle portion 1 neighboring the rigidity controller 6, the inner helical tube 8 is connected to the rigidity controller 6 such that the inner helical tube 8 can be rotated around its central axis and at the same time pushed out toward the front end of the middle portion 1 as the rigidity controller 6 is turned around, while the other helical tube 9 is immovably fixed to the rigidity controller 6.

Such a connection of the composite helical tube 7 at the rigidity controller 6 is provided by constructing the rigidity controller 6 as follows.

Figure 4:
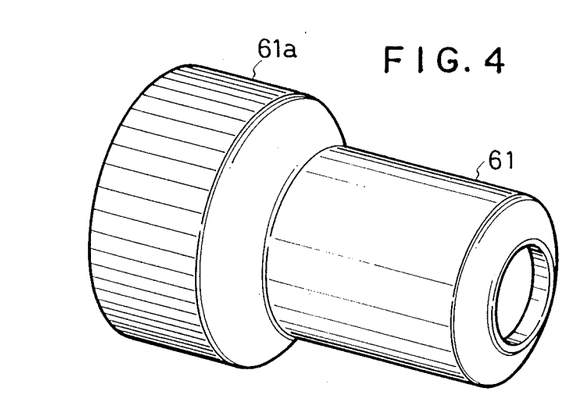
FIG. 4 is a perspective view of an outer piece of a rigidity controller of the scope section of FIG. 2.
Figure 5:
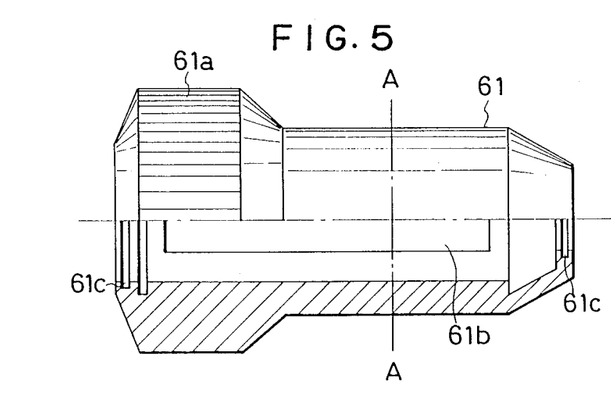
FIG. 5 is a partially cross sectional side view of the outer piece of FIG. 4.
Figure 6:
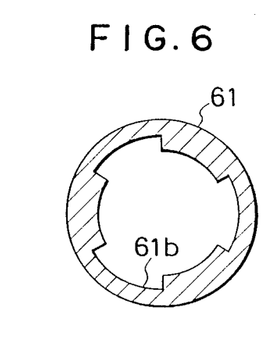
FIG. 6 is a vertical cross sectional view of the outer piece of FIG. 4 at an A—A plane shown in FIG. 5.
Figure 7:
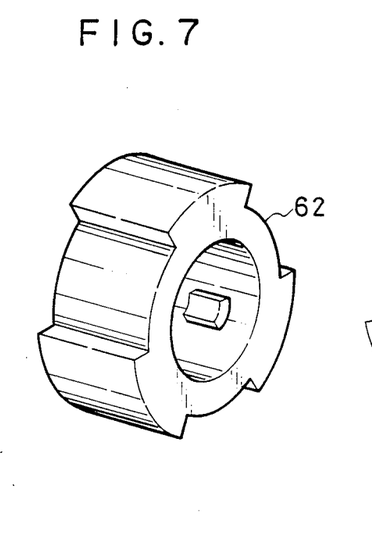
FIG. 7 is a perspective view of an intermediate piece of a rigidity controller of the scope section of FIG. 2.
Figure 8:
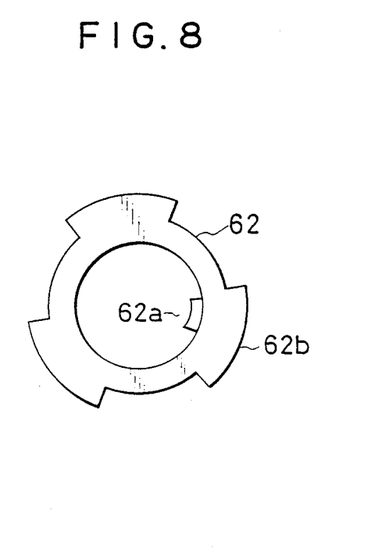
FIG. 8 is a front view of the intermediate piece of FIG. 7.
Figure 9:
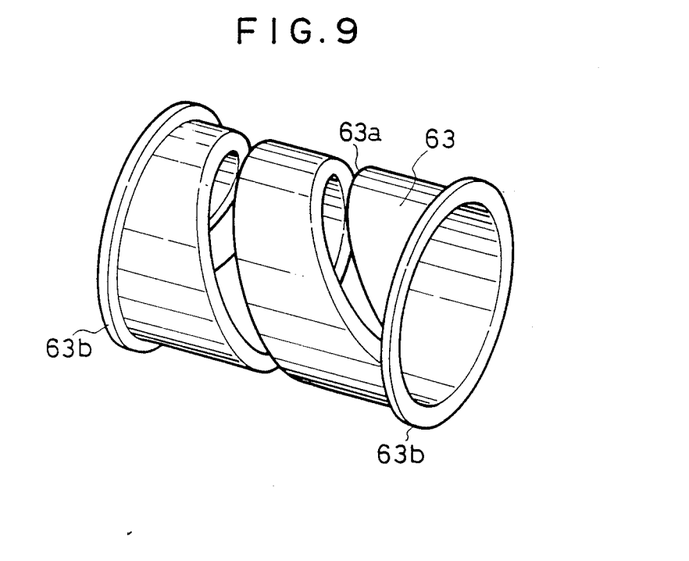
FIG. 9 is a perspective view of an inner piece of a rigidity controller of the scope section of FIG. 2.

Namely, in this embodiment, the rigidity controller 6 is constructed from an outer piece 61 shown in FIGS. 4, 5, and 6 having a knob portion 61a, engagement ports 61b and engagement grooves 61c; an intermediate piece 62 shown in FIGS. 7 and 8 having a guide portion 62a and an engagement portions 62b to be engaged with the engagement ports 61b of the outer piece 61; and an inner piece 63 shown in FIG. 9 having a loop groove 63a into which the guide portion 62a of the intermediate piece 62 is to be inserted, and engagement rims 63b to be engaged with the engagement grooves 61c of the outer piece 61. Thus, these outer piece 61, intermediate piece 62, and inner piece 63 are put together in a manner shown in FIG. 10 to form the rigidity controller 6.

Figure 10:
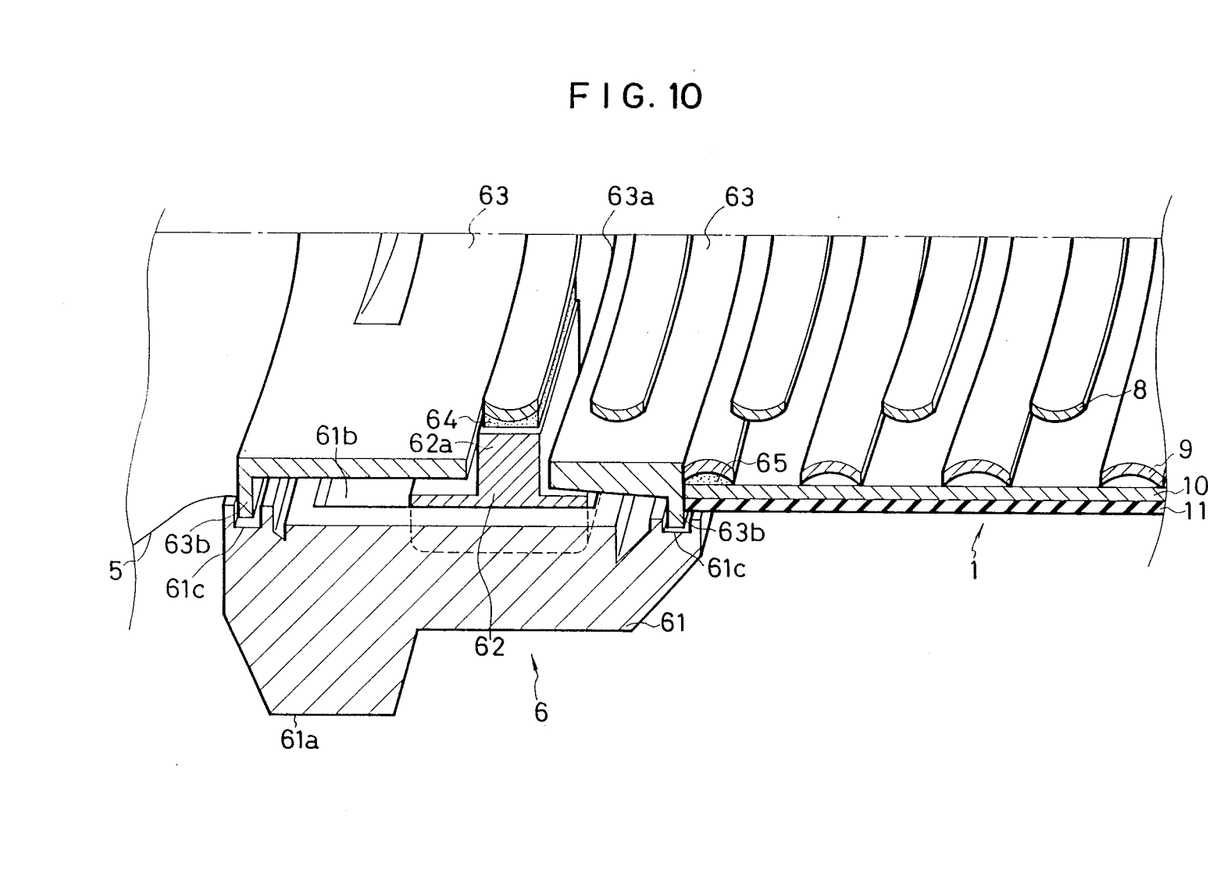
FIG. 10 is an enlarged cross sectional view of a part of a rigidity controller of the scope section of FIG. 2.

In this rigidity controller 6 so constructed, one end of the inner helical tube 8 is fixed to the guide portion 62a of the intermediate piece 62 at a fixing portion 64, while one end of the outer helical tube 9 is fixed to the inner piece 63 at a fixing portion 65.

The inner piece 63 is immovably fixed to the scope grip portion 5, so that the outer helical tube 9 is also immovably fixed.

On the other hand, the intermediate piece 62 can be rotated along the loop groove 63a of the inner piece 63 by the turning of the outer piece 61, because the intermediate piece is allowed to slide along a central axis of the middle portion 1 with respect to the outer piece 61, but not allowed to rotate with respect to the outer piece 61. Thus, when the outer piece 61 is turned around to slide the intermediate piece 62 toward the front end of the middle portion 1, the inner helical tube 8 is rotated around its central axis with respect to the outer helical tube 9, and at the same time pushed out toward the front end of the middle portion 1.

Now, in FIG. 3, the middle portion 1 in a soft state is shown for the middle portion 1 stretched out to be straight, in which the composite helical tube 7 is loosened such that the inner helical tube 8 and the outer helical tube 9 are separated from each other.

On the other hand, when the outer piece 61 of the rigidity controller 6 is turned around the slide the intermediate piece 62 of the rigidity controller 6 toward the front end of the middle portion 1, as the inner helical tube 8 is rotated around its central axis with respect to the outer helical tube 9, and at the same time pushed out toward the front end of the middle portion 1, the rigidity of the middle portion 1 is increased. Here, as the inner helical tube 8 is pushed toward the front end of the middle portion 1, the radius of the inner helical tube 8 increases, and the rigidity of the middle tube 1 increases as the interaction between the inner helical tube 8 and the outer helical tube 9 increases, as a result of a decrease of a separation between the inner helical tube 8 and the outer helical tube 9 for the middle portion 1 stretched out to be straight, until the inner helical tube 8 and the outer helical tube 9 make a tight contact with each other. It is to be noted that the winding pitch of the inner helical tube 8 is unchanged because of the push out of the inner helical tube 8 toward the front end of the middle portion 1 at the rigidity controller 6.

Figure 11:
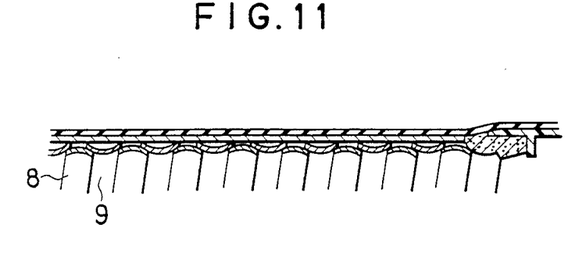
FIG. 11 is an enlarged cross sectional view of a part of a middle portion of the scope section of FIG. 2 in a hard state.

In FIG. 11, the middle portion 1 in a hard state is shown for the middle portion 1 stretched out to be straight, in which the composite helical tube 7 is tightened such that the inner helical tube 8 and the outer helical tube 9 are tightly contacting with each other.

Figure 12:
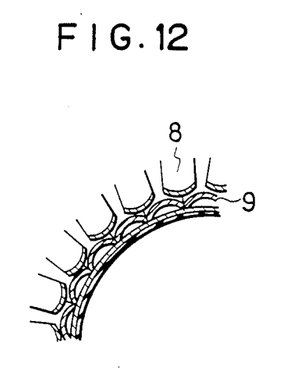
FIG. 12 is an enlarged cross sectional view of a part of a middle portion of the scope section of FIG. 2 in a soft state when the middle portion is bent.

Now, when the middle portion 1 is bent and the middle portion 1 is in the soft state, the inner helical tube 8 and the outer helical tube 9 are in a configuration shown in FIG. 12. In FIG. 12, the middle portion 1 is maximally bent, i.e., bent to have the minimum radius for an arc section formed by the middle portion 1, in which each winding of the outer helical tube 9 is in contact with the adjacent windings, so that the further bending is physically prevented. However, in this soft state, the composite helical tube 7 is loosened such that the inner helical tube 8 and the outer helical tube 9 are separated from each other, as already mentioned, so that the bending of the middle portion 1 up to the maximally bent situation shown in FIG. 12 is easier than in the hard state.

Figure 13:
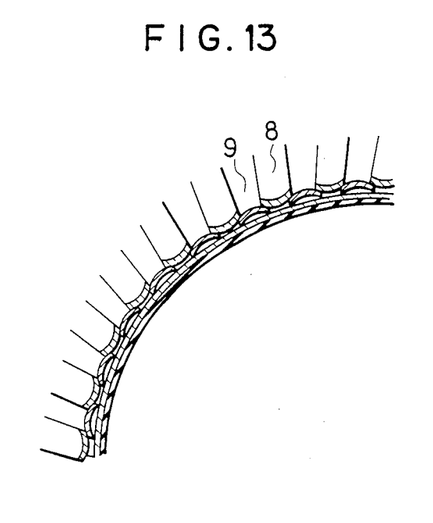
FIG. 13 is an enlarged cross sectional view of a part of a middle portion of the scope section of FIG. 2 in a hard state when the middle portion is bent.

On the other hand when the middle portion 1 is bent and the middle portion 1 is in the hard state, the inner helical tube 8 and the outer helical tube 9 are in a configuration shown in FIG. 13. In the hard state, the composite helical tube 7 is tightened such that the inner helical tube 8 and the outer helical tube 9 are tightly contacting with each other, as already mentioned, so that the bending of the middle portion 1 becomes more difficult than in the soft state.

Thus, according to this embodiment, it is possible to provide an endoscope capable of adjustably changing the rigidity of the middle portion 1.

It is to be noted that the shape of the inner helical tube 8 and the outer helical tube 9 may be changed from that of FIG. 3.

Figure 14:
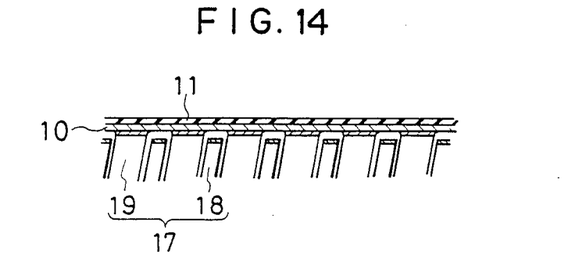
FIG. 14 is an enlarged cross sectional view of one variation for a part of a middle portion of the scope section of FIG. 2 in a soft state.

For example, the composite helical tube 7 formed by the inner helical tube 8 and the outer helical tube 9 in the above embodiment shown in FIG. 3 may be replaced, as shown in FIG. 14, by a composite helical tube 17 formed by an inner helical tube 18 and an outer helical tube 19, where the inner helical tube 18 and the outer helical tube 19 are made of a flat wiring piece.

With all the other features identical to those of the previous embodiment, the same effects can be obtained for this variation.

Thus, for this case, the middle portion 1 in a soft state is shown in FIG. 14 for the middle portion 1 stretched out to be straight, in which the composite helical tube 17 is loosened such that the inner helical tube 18 and the outer helical tube 19 are separated from each other, just as in the previous embodiment.

Figure 15:
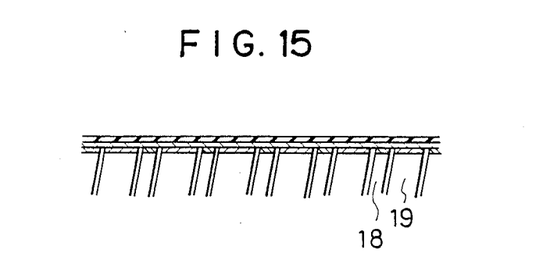
FIG. 15 is an enlarged cross sectional view of one variation for a part of a middle portion of the scope section of FIG. 2 in a hard state.

Also, the middle portion 1 in a hard state is shown in FIG. 15 for the middle portion 1 stretched out to be straight, in which the composite helical tube 17 is tightened such that the inner helical tube 18 and the outer helical tube 19 are tightly contacting with each other, just as in the previous embodiment.

Figure 16:
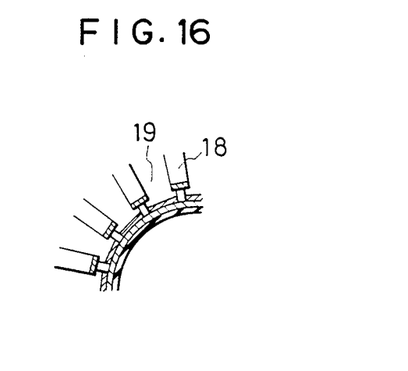
FIG. 16 is an enlarged cross sectional view of one variation of a part of a middle portion of the scope section of FIG. 2 in a soft state when the middle portion is bent.

Also, a configuration of the inner helical tube 18 and the outer helical tube 19 for the bent middle portion 1 and the middle portion 1 in the soft state is shown in FIG. 16, in which the composite helical tube 17 is loosened such that the inner helical tube 18 and the outer helical tube 19 are separated from each other, so that the bending of the middle portion 1 up to the maximally bent situation shown in FIG. 16 is easier than in the hard state, just as in the previous embodiment.

Figure 17:
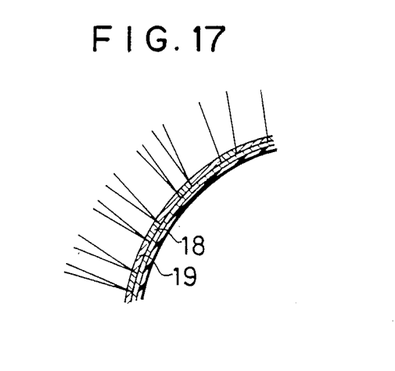
FIG. 17 is an enlarged cross sectional view of one variation for a part of a middle portion of the scope section of FIG. 2 in a hard state when the middle portion is bent.

Similarly, a configuration of the inner helical tube 18 and the outer helical tube 19 for the bent middle portion 1 and the middle portion 1 in the soft state is shown in FIG. 17, in which the composite helical tube 17 composite helical tube 17 is tightened such that the inner helical tube 18 and the outer helical tube 19 are tightly contacting with each other, so that the bending of the middle portion 1 becomes more difficult than in the soft state, just as in the previous embodiment.

It is also possible to use other shapes for the inner helical tube and the outer helical tube, so long as they can substantially function as those described above.

It is to be noted that although the composite helical tube is constructed from two helical tubes in the above embodiments, more than two helical tubes may be used for the composite helical tubes.

It is also to be noted that it is not necessary to employ the composite helical tube structure of the present invention for an entire middle portion as in the above embodiment, because a partial application of the composite helical tube structure may provide a significant advantage of making the rigidity of that portion to which the present invention is applied.

Besides these, many modifications and variations of the above embodiments may be made without departing from the novel and advantageous features of the present invention. Accordingly, all such modifications and variations are intended to be included within the scope of the appended claims.

What is claimed is:

1. An endoscope equipped with a scope section to be inserted into a body cavity of a patient, the scope section comprising:
    an end portion having an imaging device;
    a middle portion connected to the end portion, comprising:
        a composite helical tube formed by outer and inner helical tubes of different winding radii which are wound coaxially; and
        an outer covering wrapped around the composite helical tube; and
    means for controlling a rigidity of the middle portion by changing a winding radius of the inner helical tube while the outer helical tube is immovably fixed.

2. The endoscope of claim 1, wherein the outer and inner helical tubes of the composite helical tube are wound at a same particular winding pitch in a same particular winding direction.

3. The endoscope of claim 1, wherein each winding loop of each one of the outer and inner helical tubes is facing a clearance between adjacent winding loops of another one of the outer and inner helical tubes.

4. The endoscope of claim 1, wherein each one of the outer and inner helical tubes is made of a curved wiring piece having a convex side facing toward another one of the outer and inner helical tubes.

5. The endoscope of claim 1, wherein each one of the outer and inner helical tubes is made of a flat wiring piece.

6. The endoscope of claim 1, wherein the composite helical tube is immovably fixed at an end of the middle portion closer to the end portion, and the controlling means changes the winding radius of the inner helical tube by rotating the inner helical tube around a central axis of the inner helical tube and pushing the inner helical tube toward the end portion simultaneously.

7. An endoscope equipped with a scope section to be inserted into a body cavity of a patient, the scope section comprising:
    an end portion having an imaging device;
    a middle portion connected to the end portion, comprising:
        composite helical tube formed by more than one helical tubes of different winding radii which are wound coaxially; and
        outer covering wrapped around the composite helical tube; and
    means for controlling a rigidity of the middle portion by changing a winding radius of each helical tube other than an outermost helical tube while the outermost helical tube is immovably fixed.

8. The endoscope of claim 7, wherein all the helical tubes of the composite helical tube are wound at the same particular winding pitch in the same particular winding direction.

9. The endoscope of claim 7, wherein each winding loop of each helical tube is facing a clearance between adjacent winding loops of adjacent helical tube.

10. The endoscope of claim 7, wherein each helical tube is made of a curved wiring piece having a convex side facing toward an adjacent helical tube.

11. The endoscope of claim 7, wherein each helical tube is made of a flat wiring piece.

12. The endoscope of claim 7, wherein the composite helical tube is immovably fixed at an end of the middle portion closer to the end portion, and the controlling means changes the winding radius of each helical tube other than the outermost helical tube by rotating each helical tube around a central axis of each helical tube and pushing each helical tube toward the end portion simultaneously.

* * * * *